(12) United States Patent
Sabol et al.

(10) Patent No.: US 8,786,873 B2
(45) Date of Patent: Jul. 22, 2014

(54) APPLICATION SERVER FOR USE WITH A MODULAR IMAGING SYSTEM

(75) Inventors: John Michael Sabol, Sussex, WI (US); James Zhengshe Liu, Glenview, IL (US); Rajeev Ramankutty Marar, Waukesha, WI (US); Kadri Nizar Jabri, Waukesha, WI (US); Gopal Biligeri Avinash, Menomonee Falls, WI (US); Chuande Liu, Waukesha, WI (US); Tan Liu, Brookfield, WI (US)

(73) Assignee: General Electric Company, Schenectady, NY (US)

( * ) Notice: Subject to any disclaimer, the term of this patent is extended or adjusted under 35 U.S.C. 154(b) by 1310 days.

(21) Appl. No.: 12/506,067

(22) Filed: Jul. 20, 2009

(65) Prior Publication Data

US 2011/0013220 A1 Jan. 20, 2011

(51) Int. Cl.
*G06F 3/12* (2006.01)

(52) U.S. Cl.
USPC .......................... 358/1.15; 600/407; 709/218

(58) Field of Classification Search
USPC ........................................................ 358/1.15
See application file for complete search history.

(56) References Cited

U.S. PATENT DOCUMENTS

| | | |
|---|---|---|
| 5,561,611 A | 10/1996 | Avinash |
| 5,832,134 A | 11/1998 | Avinash et al. |
| 5,923,789 A | 7/1999 | Avinash |
| 5,943,433 A | 8/1999 | Avinash |
| 5,987,347 A | 11/1999 | Khoury et al. |
| 6,100,689 A | 8/2000 | Huff et al. |
| 6,118,846 A | 9/2000 | Liu |
| 6,173,083 B1 | 1/2001 | Avinash |
| 6,208,763 B1 | 3/2001 | Avinash |
| 6,246,783 B1 | 6/2001 | Avinash |
| 6,343,111 B1 | 1/2002 | Avinash et al. |
| 6,354,737 B1 | 3/2002 | Hufe et al. |
| 6,389,097 B1 | 5/2002 | Bulkes et al. |
| 6,556,720 B1 | 4/2003 | Avinash |
| 6,574,304 B1 | 6/2003 | Hsieh et al. |
| 6,579,239 B1 | 6/2003 | Avinash et al. |
| 6,580,779 B2 | 6/2003 | Avinash et al. |
| 6,588,151 B1 | 7/2003 | Goscicki et al. |
| 6,592,523 B2 | 7/2003 | Avinash et al. |
| 6,614,874 B2 | 9/2003 | Avinash |
| 6,661,873 B2 | 12/2003 | Jabri et al. |

(Continued)

FOREIGN PATENT DOCUMENTS

| | | |
|---|---|---|
| JP | 2008-080151 A | 4/2008 |
| JP | 2008-142314 A | 6/2008 |
| JP | 2008-167841 A | 7/2008 |

OTHER PUBLICATIONS

U.S. Appl. No. 11/606,672, filed Nov. 30, 2006, Choubey et al.

(Continued)

*Primary Examiner* — Benjamin O Dulaney (57) ABSTRACT

Systems and methods are disclosed for managing autonomous detector and imager subsystems communicating as nodes on a network. In an embodiment, an application server is provided which coordinates use of the autonomous imager and detector subsystems so that appropriate combinations of imagers and detectors are used for particular imaging applications. In another embodiment, the performance of a detector subsystem may be automatically evaluated prior to use, such as by one or more automated routines that monitor or measure factors related to detector performance. Additional systems, methods, and devices are also disclosed.

17 Claims, 6 Drawing Sheets

(56) References Cited

U.S. PATENT DOCUMENTS

| | | | |
|---|---|---|---|
| 6,687,329 | B1 | 2/2004 | Hsieh et al. |
| 6,701,025 | B1 | 3/2004 | Avinash |
| 6,714,623 | B2 * | 3/2004 | Sako et al. .................. 378/98.8 |
| 6,721,386 | B2 | 4/2004 | Bulkes et al. |
| 6,748,044 | B2 | 6/2004 | Sabol et al. |
| 6,757,414 | B1 | 6/2004 | Turek et al. |
| 6,757,442 | B1 | 6/2004 | Avinash |
| 6,771,736 | B2 | 8/2004 | Sabol et al. |
| 6,771,803 | B1 | 8/2004 | Turek et al. |
| 6,771,999 | B2 | 8/2004 | Salla et al. |
| 6,782,137 | B1 | 8/2004 | Avinash |
| 6,792,072 | B2 | 9/2004 | Avinash |
| 6,813,333 | B2 | 11/2004 | Karau et al. |
| 6,816,572 | B2 | 11/2004 | Jabri et al. |
| 6,836,528 | B2 | 12/2004 | Reddy et al. |
| 6,847,336 | B1 | 1/2005 | Lemelson et al. |
| 6,898,263 | B2 | 5/2005 | Avinash et al. |
| 6,917,697 | B2 | 7/2005 | Avinash et al. |
| 6,942,621 | B2 | 9/2005 | Avinash et al. |
| 6,954,516 | B2 | 10/2005 | Li et al. |
| 6,963,670 | B2 | 11/2005 | Avinash et al. |
| 6,973,219 | B2 | 12/2005 | Avinash |
| 6,980,624 | B2 | 12/2005 | Li et al. |
| 6,980,682 | B1 | 12/2005 | Avinash et al. |
| 6,996,205 | B2 | 2/2006 | Capolunghi et al. |
| 6,999,549 | B2 | 2/2006 | Sabol et al. |
| 7,016,467 | B2 | 3/2006 | Brooks |
| 7,020,343 | B1 | 3/2006 | Avinash |
| 7,050,615 | B2 | 5/2006 | Avinash et al. |
| 7,056,020 | B2 | 6/2006 | Saunders et al. |
| 7,056,707 | B2 | 6/2006 | Sattur et al. |
| 7,058,155 | B2 | 6/2006 | Piacsek et al. |
| 7,068,826 | B2 | 6/2006 | Jabri et al. |
| 7,072,435 | B2 | 7/2006 | Metz et al. |
| 7,127,026 | B2 * | 10/2006 | Amemiya et al. .............. 378/19 |
| 7,169,925 | B2 | 1/2007 | Merriman et al. |
| 7,187,790 | B2 | 3/2007 | Sabol et al. |
| 7,194,145 | B2 | 3/2007 | Avinash |
| 7,206,101 | B2 | 4/2007 | Avinash |
| 7,206,460 | B2 | 4/2007 | Avinash |
| 7,233,646 | B2 | 6/2007 | Skaberna |
| 7,248,749 | B2 | 7/2007 | Avinash et al. |
| 7,254,261 | B2 | 8/2007 | Avinash et al. |
| 7,261,465 | B2 | 8/2007 | Butzine et al. |
| 7,263,214 | B2 | 8/2007 | Uppaluri et al. |
| 7,272,429 | B2 | 9/2007 | Walker et al. |
| 7,274,811 | B2 | 9/2007 | Sirohey et al. |
| 7,295,691 | B2 | 11/2007 | Uppaluri et al. |
| 7,310,436 | B2 | 12/2007 | Li et al. |
| 7,324,628 | B2 | 1/2008 | Liu et al. |
| 7,352,885 | B2 | 4/2008 | Eberhard et al. |
| 7,359,535 | B2 | 4/2008 | Salla et al. |
| 7,359,540 | B2 | 4/2008 | Avinash |
| 7,367,953 | B2 | 5/2008 | Salla et al. |
| 7,389,136 | B2 | 6/2008 | Avinash et al. |
| 7,397,886 | B2 | 7/2008 | Avinash et al. |
| 7,414,565 | B2 | 8/2008 | Liu et al. |
| 7,415,146 | B2 | 8/2008 | Unger et al. |
| 7,418,076 | B2 | 8/2008 | Li et al. |
| 7,418,120 | B2 | 8/2008 | Weiner et al. |
| 7,433,507 | B2 | 10/2008 | Jabri et al. |
| 7,440,603 | B2 | 10/2008 | Eberhard et al. |
| 7,450,747 | B2 | 11/2008 | Jabri et al. |
| 7,457,451 | B2 | 11/2008 | Hsieh et al. |
| 7,488,947 | B1 | 2/2009 | Petrick et al. |
| 7,489,825 | B2 | 2/2009 | Sirohey et al. |
| 7,490,085 | B2 | 2/2009 | Walker et al. |
| 7,492,931 | B2 | 2/2009 | Sabol et al. |
| 7,495,228 | B1 | 2/2009 | Albagli et al. |
| 7,502,444 | B2 | 3/2009 | Marar |
| 7,508,915 | B2 | 3/2009 | Amitani et al. |
| 7,508,970 | B2 | 3/2009 | Jabri et al. |
| 7,512,284 | B2 | 3/2009 | Avinash |
| 7,519,156 | B2 | 4/2009 | Marar |
| 7,522,755 | B2 | 4/2009 | Avinash et al. |
| 7,574,032 | B2 | 8/2009 | Sirohey et al. |
| 7,575,375 | B2 | 8/2009 | Marar et al. |
| 7,589,850 | B2 | 9/2009 | Adkins et al. |
| 7,590,306 | B2 | 9/2009 | Lal et al. |
| 7,599,579 | B2 | 10/2009 | Avinash |
| 7,613,478 | B2 | 11/2009 | Jabri et al. |
| 7,620,227 | B2 | 11/2009 | Gering et al. |
| 7,623,723 | B2 | 11/2009 | Avinash |
| 7,623,728 | B2 | 11/2009 | Avinash et al. |
| 7,627,084 | B2 | 12/2009 | Jabri et al. |
| 7,627,160 | B2 | 12/2009 | Avinash et al. |
| 7,639,780 | B2 * | 12/2009 | Minyard et al. .................. 378/37 |
| 7,649,979 | B2 | 1/2010 | Liu et al. |
| 7,664,222 | B2 | 2/2010 | Jabri et al. |
| 7,702,379 | B2 | 4/2010 | Avinash et al. |
| 2002/0080918 | A1 * | 6/2002 | Sako ............................ 378/115 |
| 2003/0036693 | A1 | 2/2003 | Avinash |
| 2003/0073917 | A1 * | 4/2003 | Echauz et al. ................ 600/510 |
| 2003/0206662 | A1 | 11/2003 | Avinash |
| 2003/0215119 | A1 | 11/2003 | Uppaluri et al. |
| 2003/0215120 | A1 | 11/2003 | Uppaluri et al. |
| 2004/0022425 | A1 | 2/2004 | Avinash |
| 2004/0037475 | A1 | 2/2004 | Avinash |
| 2004/0068167 | A1 | 4/2004 | Hsieh et al. |
| 2004/0101088 | A1 | 5/2004 | Sabol et al. |
| 2004/0120558 | A1 | 6/2004 | Sabol et al. |
| 2004/0120580 | A1 | 6/2004 | Sabol et al. |
| 2004/0122702 | A1 | 6/2004 | Sabol et al. |
| 2004/0122703 | A1 | 6/2004 | Walker et al. |
| 2004/0122704 | A1 | 6/2004 | Sabol et al. |
| 2004/0122705 | A1 | 6/2004 | Sabol et al. |
| 2004/0122706 | A1 | 6/2004 | Walker et al. |
| 2004/0122707 | A1 | 6/2004 | Sabol et al. |
| 2004/0122708 | A1 | 6/2004 | Avinash et al. |
| 2004/0122709 | A1 | 6/2004 | Avinash et al. |
| 2004/0122719 | A1 | 6/2004 | Sabol et al. |
| 2004/0122787 | A1 | 6/2004 | Avinash et al. |
| 2004/0125397 | A1 * | 7/2004 | Adkins et al. ................ 358/1.14 |
| 2004/0176118 | A1 * | 9/2004 | Strittmatter et al. .......... 455/500 |
| 2004/0190032 | A1 * | 9/2004 | Ferlitsch ...................... 358/1.13 |
| 2004/0249314 | A1 | 12/2004 | Salla et al. |
| 2004/0252873 | A1 | 12/2004 | Avinash et al. |
| 2005/0005755 | A1 | 1/2005 | Turvey et al. |
| 2005/0031176 | A1 | 2/2005 | Hertel et al. |
| 2005/0110802 | A1 | 5/2005 | Avinash et al. |
| 2005/0111751 | A1 | 5/2005 | Avinash et al. |
| 2005/0113670 | A1 | 5/2005 | Salla et al. |
| 2005/0113671 | A1 | 5/2005 | Salla et al. |
| 2005/0113672 | A1 | 5/2005 | Salla et al. |
| 2005/0113674 | A1 | 5/2005 | Salla et al. |
| 2005/0152587 | A1 | 7/2005 | Sirohey et al. |
| 2005/0202844 | A1 | 9/2005 | Jabri et al. |
| 2005/0213845 | A1 | 9/2005 | Avinash et al. |
| 2005/0228273 | A1 * | 10/2005 | Tamakoshi .................... 600/425 |
| 2005/0256399 | A1 | 11/2005 | Sirohey et al. |
| 2005/0267353 | A1 * | 12/2005 | Marquart et al. ............. 600/411 |
| 2006/0008174 | A1 | 1/2006 | Avinash et al. |
| 2006/0009692 | A1 * | 1/2006 | Fukuda et al. ................ 600/407 |
| 2006/0018526 | A1 | 1/2006 | Avinash et al. |
| 2006/0050849 | A1 * | 3/2006 | Skaberna ...................... 378/118 |
| 2006/0052690 | A1 | 3/2006 | Sirohey et al. |
| 2006/0058604 | A1 | 3/2006 | Avinash et al. |
| 2006/0074713 | A1 | 4/2006 | Conry et al. |
| 2006/0133283 | A1 | 6/2006 | Weiner et al. |
| 2006/0136143 | A1 | 6/2006 | Avinash et al. |
| 2006/0136259 | A1 | 6/2006 | Weiner et al. |
| 2006/0136417 | A1 | 6/2006 | Avinash et al. |
| 2006/0136466 | A1 | 6/2006 | Weiner et al. |
| 2006/0136467 | A1 | 6/2006 | Avinash et al. |
| 2006/0143044 | A1 | 6/2006 | Conry et al. |
| 2006/0143060 | A1 | 6/2006 | Conry et al. |
| 2006/0149808 | A1 | 7/2006 | Weiner et al. |
| 2006/0149837 | A1 | 7/2006 | Weiner et al. |
| 2006/0182324 | A1 * | 8/2006 | Motoki ......................... 382/128 |
| 2006/0184489 | A1 | 8/2006 | Weiner et al. |
| 2006/0241416 | A1 * | 10/2006 | Marquart et al. ............. 600/432 |
| 2006/0242146 | A1 | 10/2006 | Piacsek et al. |
| 2006/0287593 | A1 * | 12/2006 | Jaggu et al. .................... 600/407 |
| 2006/0291711 | A1 | 12/2006 | Jabri et al. |

(56) References Cited

U.S. PATENT DOCUMENTS

| | | |
|---|---|---|
| 2007/0036419 A1 | 2/2007 | Jabri et al. |
| 2007/0052716 A1 | 3/2007 | Jabri et al. |
| 2007/0078873 A1 | 4/2007 | Avinash et al. |
| 2007/0081699 A1 | 4/2007 | Avinash et al. |
| 2007/0081700 A1 | 4/2007 | Blumenfeld et al. |
| 2007/0081701 A1 | 4/2007 | Sirohey et al. |
| 2007/0081707 A1 | 4/2007 | Sirohey et al. |
| 2007/0116348 A1 | 5/2007 | Jabri |
| 2007/0118399 A1* | 5/2007 | Avinash et al. ............ 705/2 |
| 2007/0127789 A1 | 6/2007 | Hoppel et al. |
| 2007/0133851 A1 | 6/2007 | Sirohey et al. |
| 2007/0156450 A1* | 7/2007 | Roehm et al. ............. 705/2 |
| 2007/0156626 A1 | 7/2007 | Roehm et al. |
| 2007/0165141 A1 | 7/2007 | Srinivas et al. |
| 2007/0165920 A1 | 7/2007 | Gering et al. |
| 2007/0286527 A1 | 12/2007 | Jabri et al. |
| 2008/0008372 A1 | 1/2008 | Li et al. |
| 2008/0008373 A1 | 1/2008 | Sirohey et al. |
| 2008/0021301 A1 | 1/2008 | Gonzalez et al. |
| 2008/0025583 A1 | 1/2008 | Jabri et al. |
| 2008/0031507 A1 | 2/2008 | Uppaluri et al. |
| 2008/0037846 A1 | 2/2008 | Avinash et al. |
| 2008/0037847 A1 | 2/2008 | Avinash et al. |
| 2008/0064949 A1 | 3/2008 | Hertel et al. |
| 2008/0095462 A1 | 4/2008 | Hsieh et al. |
| 2008/0108895 A1 | 5/2008 | Sabol et al. |
| 2008/0118021 A1 | 5/2008 | Dutta et al. |
| 2008/0118111 A1 | 5/2008 | Sirohey et al. |
| 2008/0118121 A1 | 5/2008 | Skinner et al. |
| 2008/0118122 A1 | 5/2008 | Sirohey et al. |
| 2008/0118127 A1 | 5/2008 | Sirohey et al. |
| 2008/0118131 A1 | 5/2008 | Skinner et al. |
| 2008/0119713 A1 | 5/2008 | Nezet et al. |
| 2008/0122842 A1 | 5/2008 | Sirohey et al. |
| 2008/0123812 A1 | 5/2008 | Sabol et al. |
| 2008/0123912 A1* | 5/2008 | Lal et al. ............. 382/128 |
| 2008/0126118 A1 | 5/2008 | Sirohey et al. |
| 2008/0126119 A1 | 5/2008 | Sirohey et al. |
| 2008/0126120 A1 | 5/2008 | Sirohey et al. |
| 2008/0126121 A1* | 5/2008 | Sirohey et al. ............ 705/2 |
| 2008/0130965 A1 | 6/2008 | Avinash et al. |
| 2008/0137926 A1 | 6/2008 | Skinner et al. |
| 2008/0154744 A1* | 6/2008 | Amitani et al. ............ 705/26 |
| 2008/0161672 A1* | 7/2008 | Marar ............. 600/407 |
| 2008/0212839 A1 | 9/2008 | Salla et al. |
| 2008/0224056 A1 | 9/2008 | Liu et al. |
| 2008/0231910 A1 | 9/2008 | Gering et al. |
| 2008/0232553 A1* | 9/2008 | Agano et al. ............ 378/197 |
| 2008/0232699 A1 | 9/2008 | Gering et al. |
| 2008/0232700 A1 | 9/2008 | Gering et al. |
| 2008/0232701 A1 | 9/2008 | Gering et al. |
| 2008/0232718 A1 | 9/2008 | Avinash et al. |
| 2008/0240343 A1 | 10/2008 | Jabri et al. |
| 2008/0240357 A1 | 10/2008 | Jabri et al. |
| 2008/0240360 A1 | 10/2008 | Jabri |
| 2008/0242977 A1 | 10/2008 | Sirohey et al. |
| 2008/0247513 A1* | 10/2008 | Amitani et al. ............ 378/95 |
| 2008/0285711 A1 | 11/2008 | Avinash et al. |
| 2008/0285712 A1* | 11/2008 | Kopans et al. ............ 378/26 |
| 2008/0296507 A1 | 12/2008 | Petrick et al. |
| 2009/0003679 A1 | 1/2009 | Ni et al. |
| 2009/0006131 A1 | 1/2009 | Unger et al. |
| 2009/0006132 A1 | 1/2009 | Avinash et al. |
| 2009/0060310 A1 | 3/2009 | Li et al. |
| 2009/0063186 A1 | 3/2009 | Marar |
| 2009/0067667 A1 | 3/2009 | Jabri |
| 2009/0092307 A1 | 4/2009 | Sabol et al. |
| 2009/0103679 A1 | 4/2009 | Jabri et al. |
| 2009/0118606 A1* | 5/2009 | Jabri et al. ............ 600/407 |
| 2009/0129547 A1 | 5/2009 | Jabri et al. |
| 2009/0130983 A1 | 5/2009 | Venturino et al. |
| 2009/0136096 A1 | 5/2009 | Sirohey et al. |
| 2009/0136111 A1 | 5/2009 | Jabri et al. |
| 2009/0138279 A1 | 5/2009 | Avinash et al. |
| 2009/0169073 A1 | 7/2009 | Areste et al. |
| 2009/0169074 A1 | 7/2009 | Avinash et al. |
| 2009/0232278 A1* | 9/2009 | Ohara ............ 378/116 |
| 2009/0257628 A1 | 10/2009 | Ranga et al. |
| 2009/0279752 A1 | 11/2009 | Sirohey et al. |
| 2009/0279759 A1 | 11/2009 | Sirohey et al. |
| 2009/0281423 A1 | 11/2009 | Sirohey et al. |
| 2009/0290686 A1 | 11/2009 | Liu et al. |
| 2009/0290772 A1 | 11/2009 | Avinash et al. |
| 2009/0292203 A1* | 11/2009 | Amemiya ............ 600/437 |
| 2009/0292478 A1 | 11/2009 | Avinash et al. |
| 2009/0292551 A1 | 11/2009 | Sirohey et al. |
| 2009/0292557 A1 | 11/2009 | Sirohey et al. |
| 2010/0004023 A1 | 1/2010 | Jabri et al. |
| 2010/0020933 A1* | 1/2010 | Topfer et al. ............ 378/98.11 |
| 2010/0046705 A1 | 2/2010 | Jabri et al. |
| 2010/0082506 A1 | 4/2010 | Avinash et al. |
| 2010/0169423 A1* | 7/2010 | Eguchi ............ 709/204 |
| 2010/0174180 A1* | 7/2010 | Rousso et al. ............ 600/431 |

OTHER PUBLICATIONS

U.S. Appl. No. 12/123,824, filed May 20, 2008, Sirohey et al.
U.S. Appl. No. 12/123,947, filed May 20, 2008, Sirohey et al.
U.S. Appl. No. 12/123,911, filed May 20, 2008, Avinash et al.
U.S. Appl. No. 12/123,918, filed May 20, 2008, Avinash et al.
U.S. Appl. No. 12/124,355, filed May 21, 2008, Liu et al.
U.S. Appl. No. 12/242,319, filed Sep. 30, 2008, Avinash et al.
U.S. Appl. No. 12/274,220, filed Nov. 19, 2008, Petrick et al.
U.S. Appl. No. 12/356,488, filed Jan. 20, 2009, Lamberty et al.
U.S. Appl. No. 12/403,551, filed Mar. 13, 2009, Liu et al.
U.S. Appl. No. 12/414,848, filed Mar. 13, 2009, Liu et al.
U.S. Appl. No. 61/181,567, filed May 27, 2009, Avinash et al.
U.S. Appl. No. 12/776,207, filed May 7, 2010, Jon Charles Omernick et al.
U.S. Appl. No. 12/776,166, filed May 7, 2010, Kadri Nizar Jabri et al.
French preliminary Search Report achieved Jul. 24, 2013; French Application No. FR 10 55654; 5 pages.
Unofficial translation of Japanese Office Action for Japanese Application No. 2010-156344, dated Jan. 28, 2014.

\* cited by examiner

APPLICATION SERVER FOR USE WITH A MODULAR IMAGING SYSTEM

BACKGROUND

The present disclosure generally relates to digital imaging systems, and particularly to management of modular imaging systems.

A number of radiological imaging systems of various designs are known and are presently in use. Certain of these systems are based upon generation of X-rays that are directed toward a subject of interest. The X-rays traverse the subject and impact a film or a digital detector. In medical diagnostic contexts, for example, such systems may be used to visualize internal tissues and diagnose patient ailments. In other contexts, parts, baggage, parcels, and other subjects may be imaged to assess their contents and for other purposes.

Current imaging subsystems typically include specific components for X-ray generation and shaping (e.g., imager components) and for X-ray detection that are configured to function with one another. That is, a detector generally cannot function without the associated and compatible imager subsystem. Similarly, the imager subsystem is typically not functional without the associated and compatible detector. As a result, even if a detector and corresponding imager subsystem are not structurally attached, a given detector and/or imager subsystem may be limited to use with one another.

Furthermore, particular imaging applications may be enabled on an imaging system based on the capabilities and/or properties of the imager subsystem and detector. Thus, a particular combination of an imager subsystem and detector may be suitable for specific applications, e.g., imaging protocols, examinations, and so forth. Such applications may, therefore, be fixed, i.e., static, for a given detector and imager subsystem. The need to know what applications may be performed for a given detector and imager subsystem may, therefore, also act to limit the use of a detector with a given imager subsystem.

BRIEF DESCRIPTION

Certain aspects commensurate in scope with the originally claimed invention are set forth below. It should be understood that these aspects are presented merely to provide the reader with a brief summary of certain forms the invention might take and that these aspects are not intended to limit the scope of the invention. Indeed, the invention may encompass a variety of aspects that may not be set forth below.

Some embodiments of the present invention may generally relate to an imaging management system. The image management system may include a network and a plurality of autonomous imager subsystems, each capable of communicating as a node on the network. The image management system may also include a plurality of autonomous detector subsystems, each capable of communicating as a node on the network. In addition, the image management system may also include an application server capable of communicating as a node on the network. The application server stores and executes routines that generate combinations of imagers and detectors from the plurality of autonomous imager subsystems and the plurality of autonomous detector subsystems based on an application to be performed.

In another embodiment, an imaging management system is provided. The image management system may include a network and a plurality of autonomous imager subsystems, each capable of communicating as a node on the network. The image management system may also include a plurality of autonomous detector subsystems, each capable of communicating as a node on the network. In addition, the image management system may also include an application server capable of communicating as a node on the network. The application server stores and executes routines that determine and indicate available applications for different combinations of imagers and detectors from the plurality of autonomous imager subsystems and the plurality of autonomous detector subsystems.

In a further embodiment, a method is provided for monitoring detector performance. In accordance with this method, one or more routines are executed to determine the operational status of an autonomous wireless detector. A device in wireless communication with the autonomous wireless detector is notified as to the operation status of the autonomous wireless detector Various refinements of the features noted above may exist in relation to various aspects of the present invention. Further features may also be incorporated in these various aspects as well. These refinements and additional features may exist individually or in any combination. For instance, various features discussed below in relation to one or more of the illustrated embodiments may be incorporated into any of the above-described aspects of the present invention alone or in any combination. Again, the brief summary presented above is intended only to familiarize the reader with certain aspects and contexts of the present invention without limitation to the claimed subject matter.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

One or more specific embodiments of the present invention will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Moreover, while the term "exemplary" may be used herein in connection to certain examples of aspects or embodiments of the presently disclosed technique, it will be appreciated that these examples are illustrative in nature and that the term "exemplary" is not used herein to denote any preference or requirement with respect to a disclosed aspect or embodiment. Further, any use of the terms "top," "bottom," "above," "below," other positional terms, and variations of these terms is made for convenience, but does not require any particular orientation of the described components.

Figure 1:
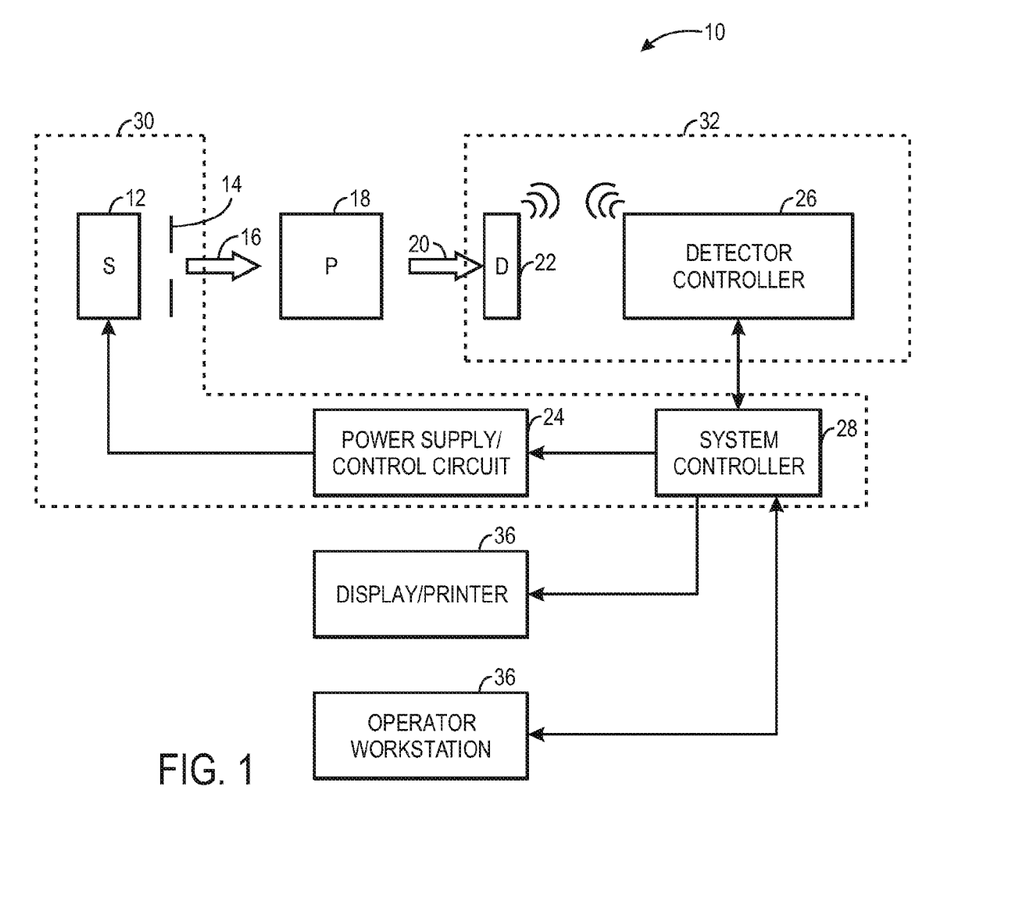
FIG. 1 is a diagrammatical overview of a digital X-ray imaging system of one embodiment in which the present technique may be utilized.

Turning now to the drawings, FIG. 1 illustrates diagrammatically an imaging system 10 for acquiring and processing discrete pixel image data. In the illustrated embodiment, the imaging system 10 is a digital X-ray system designed both to acquire original image data and to process the image data for display in accordance with the present technique. In the embodiment illustrated in FIG. 1, imaging system 10 includes a source of X-ray radiation 12 positioned adjacent to a collimator 14. The collimator 14 permits a stream of radiation 16 to pass into a region in which an object or subject, such as a patient 18, is positioned. In certain embodiments a filter may also be present to filter the X-ray radiation. A portion of the radiation 20 passes through or around the subject and impacts a digital X-ray detector, represented generally at reference numeral 22. As will be appreciated by those skilled in the art, the detector 22 may convert the X-ray photons received on its surface to lower energy photons, and subsequently to electric signals, which are acquired and processed to reconstruct an image of the features within the subject.

The radiation source 12 is controlled by a power supply/control circuit 24 which supplies both power and control signals for examination sequences. The detector 22 is communicatively coupled to a detector controller 26 which commands acquisition of the signals generated in the detector 22. In the presently illustrated embodiment, the detector 22 may communicate with the detector controller 26 via any suitable wire or wireless communication standard. In certain embodiments, some or all of the functions of the detector controller 26 may be integrated within a structure that also houses the detector 22, i.e., the detector controller 26 and detector 22 may be provided as a unitary device. The detector controller 26 may, among other functions, execute various signal processing and filtration functions, such as for initial adjustment of dynamic ranges, interleaving of digital image data, and so forth.

In the depicted embodiment the power supply/control circuit 24 and the detector controller 26 may communicate with, and respond to signals from, a system controller 28. In general, the system controller 28 commands operation of the imaging system to execute examination protocols and to process acquired image data. In the present context, the system controller 28 also includes signal processing circuitry (typically based upon a programmed general purpose or application-specific digital computer) and associated manufactures (such as optical memory devices, magnetic memory devices, or solid-state memory devices) for storing programs and routines executed by a processor of the computer to carry out various functionalities, as well as for storing configuration parameters and image data and so forth.

In one embodiment, different components of the imaging system 10 may be provided as autonomous and separable subsystems. For example, some or all of the source 12, collimator 14, and/or power supply/control circuit 24 may be provided as an imager subsystem 30. Likewise, the detector 22 may be provided as an autonomous and separable detector subsystem 32. In the depicted embodiment, the autonomous detector subsystem 32 includes a detector controller 26, which may be provided integrally with the detector 22. In other embodiments, the detector controller 26 may be provided separately from the detector 22 (such as on a downstream workstation or server or as part of the system controller 28, discussed below) or may be distributed such that aspects of the detector controller 26 are provided on the detector 22 while other aspects are provided downstream). In this manner, either of the autonomous imager subsystem 30 or the autonomous detector subsystem 32 may be exchanged for a different source or detector subsystem, having the same or different capabilities, in a dynamic imaging environment.

In the depicted embodiment, the system controller 28 is shown as being part of the imager subsystem 30. However, in other embodiments, the system controller 28 may be a stand alone component or subsystem or may be part of the detector subsystem 32. In other embodiments, the functions, hardware, and/or software of the system controller 28 may be distributed so that different hardware, software, and/or firmware aspects of the system controller 28 are appropriately distributed between the imager subsystem 30, the detector subsystem 32, and/or a separate and distinct control subsystem. In this manner, the source, detection, and/or control functions of the imaging system 10 may be provided by completely or partially autonomous subsystems which can be treated as modular components, i.e., one detector subsystem 32 or imager subsystem 30 may be swapped for another to provide different respective detection or X-ray source functionality.

As used herein, the term "autonomous" describes a system or subsystem that has communication capability even when it is not connected or associated with a complementary subsystem of the imaging system 10. For example, the phrase "autonomous detector subsystem" describes a detection system that has communication capability with a network, such as server, even when it is not connected or associated with an imager subsystem 10. Further, in one embodiment, an autonomous detector subsystem 32 may provide communication capability (such as with a second autonomous imager subsystem 30 or a second network) even when it is associated with an autonomous imager subsystem 30.

Stated differently, an autonomous system component may be independently operable in terms of its system design, system implementation, application deployment, and/or service. Such autonomous components may be configured for and capable of use with more than one other complementary or counterpart autonomous component. Accordingly, in one embodiment, each of the main components (e.g., the autonomous imager subsystem 30 and the autonomous detector subsystem 32) may be considered as network nodes that operate as autonomous entities in a network environment. In such an environment, different types of autonomous imager and/or detector subsystems (such as from the same or different vendors, having the same or different capabilities and/or sizes, and so forth) can be used in various combinations in forming an imaging system 10.

In the depicted embodiment of FIG. 1, the system controller 28 is linked to at least one output device, such as a display or printer as indicated at reference numeral 34. The output device may include standard or special purpose computer monitors and associated processing circuitry. One or more operator workstations 36 or servers may be further linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

Figure 2:
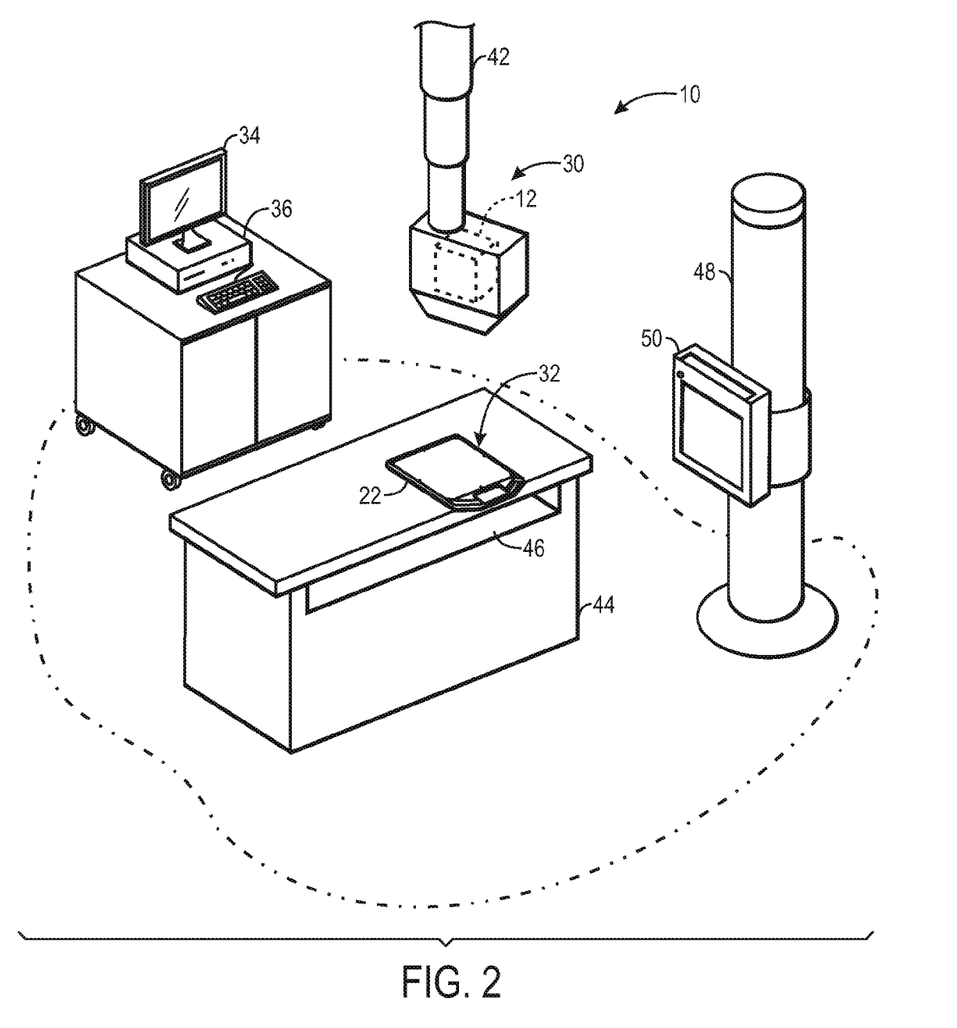
FIG. 2 is a perspective view of the digital X-ray imaging system of FIG. 1 in accordance with one embodiment.

By way of further example, a perspective view of an imaging system 10 is provided in FIG. 2. The imaging system 10 includes a positioning component in the form of an overhead tube support arm 42 for positioning a radiation source 12, such as an X-ray tube, with respect to a patient 18 and a detector 22. In other embodiments, the radiation source 12 may be provided on a C-arm or other rotating structure to allow activation of the radiation source 12 at various angular positions. For example, in one such embodiment, the C-arm or other rotating structure may allow radiation source activation over a limited angular range (e.g., 20°, 45°, 90°, or 120°), over 180° of rotation, or over 360° of rotation. Such embodiments may be useful for tomosynthesis applications (where data acquisition involves acquiring discrete images over a limited angular range) or for C-arm angiography. Thus, in the depicted embodiment, an autonomous imager subsystem 30 may include the source 12, and may or may not include positioning subsystems (such as the arm 42 or a C-arm), power supply/control circuitry, and/or system control circuitry (such as may be provided as part of the source 12 or as part of a workstation 36 or server in communication with the source 12. In certain embodiments, the source 12 and/or imager subsystem 30 may receive instructions (such as from workstation 36) via a wired connection (such as an Ethernet cable) or via a wireless connection (such as via a wireless transceiver). It is noted that such a wireless transceiver may utilize any suitable wireless communication protocol, such as an ultra wideband (UWB) communication standard, a Bluetooth communication standard, or any 802.11 communication standard.

The depicted imaging system 10 includes a portable digital detector 22 that may operate autonomously from the source 12. In the depicted embodiment, the digital detector 22 is all or part of a detector subsystem 32, as described herein. In various embodiments, the detector 22 may be powered by a rechargeable battery (which may or may not also be removable) and may communicate data via a wireless connection, such as via a wireless transceiver utilizing a suitable wireless communication protocol. Alternatively, in other embodiments, the detector 22 may receive power and/or transmit data via a wire or cable, i.e., a tether. In embodiments in which the tether provides power to the detector 22 and data transfer from the detector 22, the cable may include respective conductors for power and data.

The digital detector 22 may also include one or more processor components and/or a memory device capable of storing image data acquired and/or programs, routines or protocols to be executed by the one or more processing components. For example, in various embodiments, the memory device may include an optical memory device, a magnetic memory device, or a solid state-memory device. Additionally, in at least one embodiment, the memory device may be a non-volatile memory device, such as a flash memory. In one embodiment, processing components located in the detector 22 may execute routines stored in the detector 22 that provide some or all of the functionality of the detector controller 26.

Also depicted in FIG. 2 is a workstation 36 and display 34 that may be in communication with one or both of the autonomous imager subsystem 30 and autonomous detector subsystem 32 of the imaging system 10. In one embodiment, the workstation 36 may include or provide the functionality of the system controller 28 such that at user, by interacting with the workstation 36 may control operation of the source 12 and detector 22. In other embodiments, the functions of the system controller 28 may be decentralized, such that some functions of the system controller 28 are performed at the workstation 36, while other functions are performed by one or more of the imager subsystem 30 and/or the detector subsystem 32. In one embodiment, the workstation 36 may be configured to function as a server of instructions and/or content on a network, such as a hospital information system (HIS), a radiology information system (RIS), and/or picture archiving communication system (PACS). In such embodiments, the workstation 36 may be construed to be a server or one or more virtual servers (i.e., server routines or applications) may be executed on the workstation 36 such that the workstation 36 may provide the functionality of one or more that one server device or application. For example, the workstation 36 may include a memory, such as an optical, magnetic, or solid state memory device, that stores server routines which, when executed by a processing component of the workstation 36, provide the application server functionality described herein.

In an embodiment, the imaging system 10 may be used with one or both of a patient table 44 and a wall stand 48 to facilitate image acquisition. Particularly, the table 44 and the wall stand 48 may be configured to receive one or more digital detectors 22. For instance, a digital detector 22 may be placed on the upper surface of the table 44, and the patient 18 (more specifically, an anatomy of interest of the patient 18) may be positioned on the table 44 between the detector 22 and the radiation source 12. In some other instances, the detector 22 may be positioned in a slot 46 below the upper surface of the table 44 and the patient 18, or the radiation source 12 and the detector 22 may be positioned horizontally about the patient 18 for cross-table imaging. Further, the wall stand 48 may include a receiving structure 50 also adapted to receive the digital detector 22, and the patient 18 may be positioned adjacent the wall stand 48 to enable image data to be acquired via the digital detector 22.

In one embodiment, the imaging system 10 may be a stationary system disposed in a fixed X-ray imaging room, such as that generally depicted in, and described above with respect to, FIG. 2. It will be appreciated, however, that the presently disclosed techniques may also be employed with other imaging systems, including mobile X-ray units and systems, in other embodiments. For instance, in other embodiments, a mobile X-ray unit may be moved to a patient recovery room, an emergency room, a surgical room, or the like to enable imaging of a patient without requiring transport of the patient to a dedicated (i.e., fixed) X-ray imaging room.

With the foregoing uses in mind, in one embodiment, one or more of the autonomous imager subsystem 30, the detector subsystem 32, and/or the workstation 36 may be provided as a node on a network, such as the HIS, RIS, and/or PACS noted above. For example, one or more of the workstation 36, the imager subsystem 30, and/or the detector subsystem 32 may be operate or communicate with one another (or with other nodes on the respective network) via respective wireless or wired network connections. In this manner, the detector subsystem 32 may communicate acquired image data to either the imager subsystem 30 or the workstation 36 via a wired or wireless network connection. Likewise, the workstation 36 may communicate with and/or control one or both of the imager subsystem 30 or the detector subsystem 32 via a wired or wireless network connection. Similarly, the imager subsystem 30 may communicate with the workstation 36 or the detector subsystem 32 via a wired or wireless network connection. In such a networked embodiment, the autonomous components (e.g., the imager subsystem 30, the detector subsystem 32, and the workstation 36) may operate independently and thus may communicate among themselves or with other devices on the network independent of one another. For example, the detector 22 may communicate with the depicted workstation 36 over a network connection and may also communicate with another workstation or server on the network instead of or in addition to the workstation 36 associated with the detector 22 in a given imaging system 10.

In one such embodiment, the workstation 36 may function as an application server (either as a hardware or virtual implementation of an application server). In such an embodiment, communication between the detector 22 and the workstation 36, or another respective server on the network, allows unimpeded data storage, detector registration, and location identification while the detector 22 is being used with the imaging subsystem 10 for imaging. In a similar fashion, direct communication between the imager subsystem 30 and the workstation 36, or another respective server on the network, allows determination of a suitable detector 22 for a particular application, as well as transfer of calibration files, software, and firmware upgrades to the imager subsystem 30.

Figure 3:
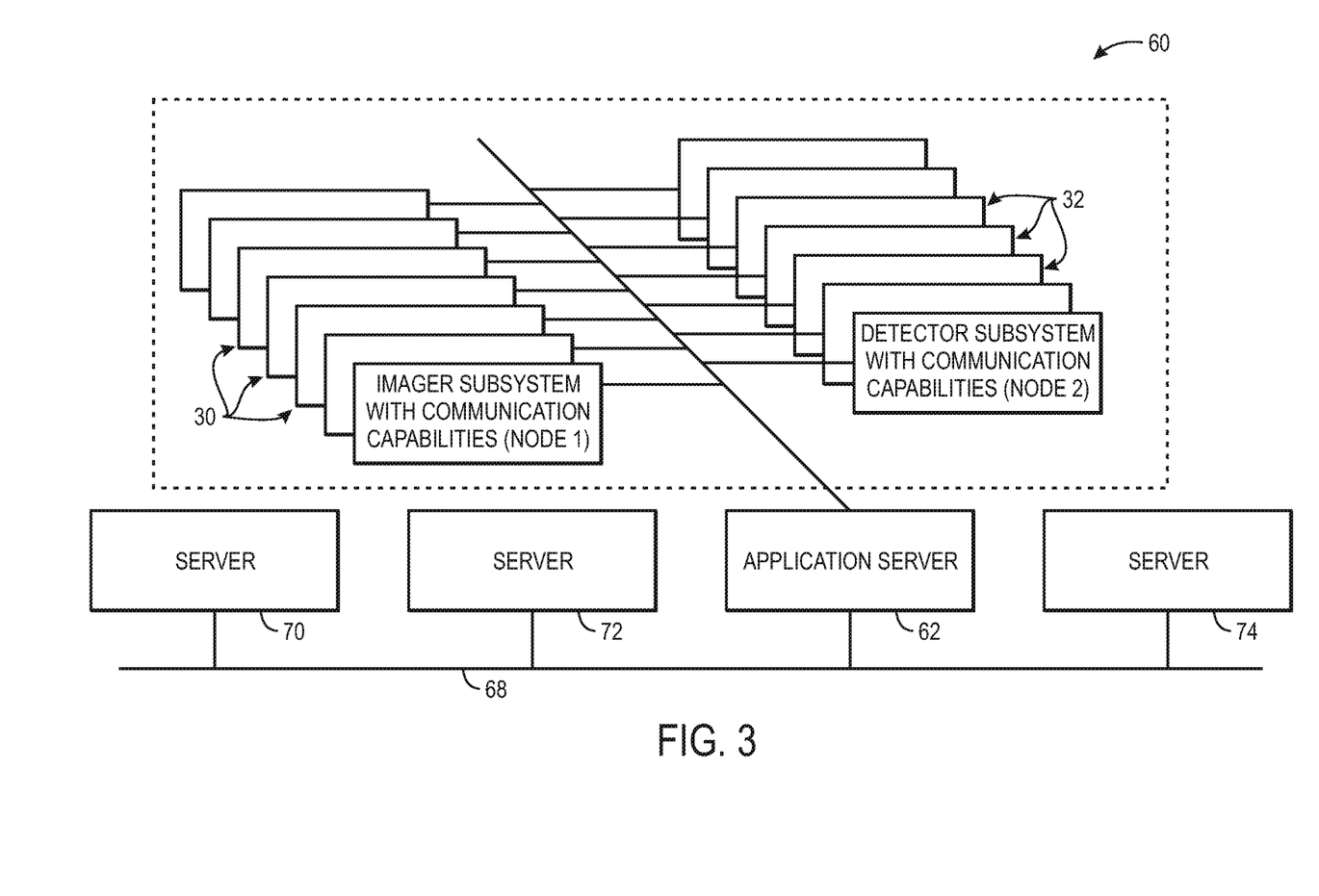
FIG. 3 is a block diagram of a network environment having autonomous detector subsystems and autonomous imager subsystems as nodes in accordance with one embodiment.

Referring now to FIG. 3, an embodiment of a distributed network system 60 is depicted. In an embodiment, more than one imager subsystem 30 and detector subsystem 32 may be present on the network 60 and in communication with an application server 62. Each imager subsystems 30 and/or detector subsystem 32 may be capable of operating independent of one another and thus may form different combinations of paired imager and detector subsystems, as discussed herein. In an embodiment, the application server 62 is in communication via a distributed network 68, such as a hospital information system (HIS) or a radiology information system (RIS) with servers 70, 72, and 74. Furthermore, by communicating with one or more detector subsystems 32 and one or more imager subsystems 30, the application server 62 may maintain standardized image acquisition protocols, including calibration procedures and methods, throughout the distributed network 68. In an embodiment, the distributed network 68 includes a connection to the Internet, to thereby allow remote access to the autonomous components of the imaging system 10, to transfer data for remote diagnostic and service upgrade purposes for example.

In one embodiment, the application server 62 may determine which applications are available and enabled on any given combination of autonomous detector subsystem 32 and imager subsystem 30. As discussed in greater detail below, an application server 62 may interact with a HIS or RIS system to assist in scheduling procedures. In such embodiments, the application server 62 may be used to match available detector subsystems 32, imager subsystems 30, examination rooms or other facilities, personnel, and/or applications with one or more requested procedures, such as may be submitted to the application server via a HIS or RIS system. In this manner, the application server 62 may ensure detector subsystems 32 and imager subsystems 30 with the appropriate properties are available and used for a given application. For example, in one implementation, the application server 62 may query a connected HIS or RIS for a list of scheduled procedures than may match available or known imager subsystems 30, detector subsystems 32, and/or other information (rooms, personnel and qualifications, and so forth) based on the list of scheduled procedures. The matched subsystems, rooms, personnel, and so forth may then be provided over the network such that this information is available over the network to the technologists that perform the exams. In this manner, a respective technologist may know what subsystems to use in performing a procedure and, in some embodiments, where and when to perform the procedure. For example, the application server 62 may generate imager/detector subsystems pairs and then may display or provide these pairs at detector docking stations or workstations so that a technologist can retrieve an appropriate detector subsystem 32 for a scheduled exam. Likewise, the application server 62, based on a selected imager subsystem 30 and a selected detector subsystem 32, may provide a list of what applications the selected imager/detector subsystems pair can be used to perform.

Figure 4:
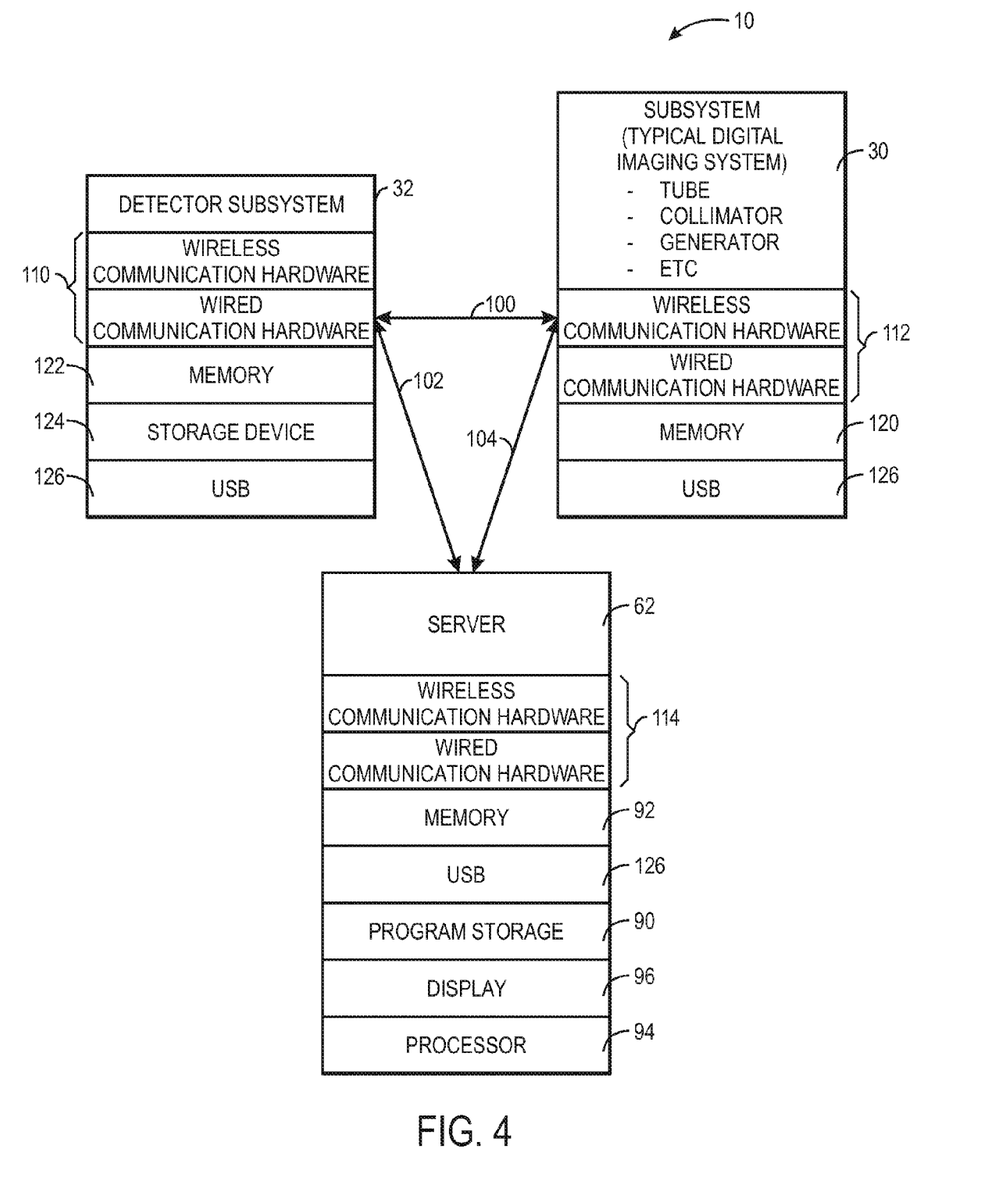
FIG. 4 is a block diagram of the components of a detector subsystem, an imager subsystem, and an application server in accordance with one embodiment.

Referring now to FIG. 4, an embodiment of an imaging system 10 is depicted in block form to provide greater detail related to the individual components, e.g., detector subsystem 32, and imager subsystem 30, and the components of an associated application server 62. A purpose of the imaging system 10, in addition to normal imaging tasks, may be to provide access to shared resources, such as data and information related to the imager subsystem 30 and detector subsystem 32 that may reside on the application server 62.

In one embodiment, the application server 62, or a suitable computing platform on which a virtual application server package is implemented, may include one or more storage devices 90, such as solid state or magnetic disk drives, optical disks, or other magnetic, solid state, or optical media, that may store system, data, application, and electronic communication files. Applications, data, and/or routines stored on a storage device 90 (such as routines for implementing an application server as discussed herein) may be transferred to a memory 92 prior to being processed by a processor 94. The application server 62 may also include or be in communication with an output device, such as a CRT or LCD display screen 96 suitable for an operator to interact with operating systems, virtual servers, and/or applications running on the application server 62.

The autonomous imager subsystem 30 and detector subsystem 32 can be configured to communicate with each other via primary-networking components such as network interconnection 100, via suitable network communication, such as conductive wire or fiber optic network cables or infrared or radio wireless connections. Similarly, autonomous imager subsystem 30 and autonomous detector subsystem 32 can be configured to communicate with the application server 62 via respective network interconnections 102, 104 For example, in one embodiment, the application server 62, imager subsystem 30, and detector subsystem 32 each includes Network Interface Circuitry (NIC) 110, 112, 114 (also herein referred to as an "interface") which allows communication between the respective component and a network on which the other imaging system 10 components are also nodes.

The respective NICs 110, 112, 114 may include, for example, circuitry to support wired communication such as Ethernet, serial, and universal serial bus (USB) 126 connections, as well as circuitry to support wireless communication, such as versions of 802.11 or Bluetooth. Additionally, the NICs 110, 112, 114 may support communication between the detector subsystem 32 and imager subsystem 30 directly as well as with the application server 62. Likewise, the NICs 110, 112, 114 may support communication between the components of the imaging system 10 via a global communication network, such as the Internet. Any or all of the NICs 110, 112, 114 may be part of a motherboard associated with the respective devices or may be provided via a separate plug-in card to maximize flexibility. Any of the imager subsystem 30, detector subsystem 32, and/or application server 62 may include one or more memory components 92, 120, 122, such as CompactFlash™ (commercially available from SanDisk Corporation, Milpitas, Calif.), synchronous dynamic random access memory (SDRAM), or other suitable memory components, as well as a storage devices 90, 124, such as a hard disk drive for long term memory storage, for example.

In one embodiment, the NIC circuitry 110 of the detector subsystem 32 may allow the transfer of data from the detector subsystem 32 to the imager subsystem 30 or the application server 62 via at least one of the interconnections 100, 102. In one embodiment, the NIC circuitry 110 is responsive to direct physical signal connection with the imager subsystem 30. In another embodiment, the NIC circuitry 110 is responsive to signal connection to the imager subsystem 30 via the application server 62. In one embodiment, the imager subsystem 30 may receive data from more than one detector subsystem 32 and may generate a signal confirming compatibility of the imager subsystem 30 with at least one of the available detector subsystems 32, based upon the signal. Examples of data that may be transferred include, but are not limited to, functionally descriptive properties, image data, text data, waveform data, video data, audio data, and control signals.

The network interconnections 100, 102, 104 allow software on the individual detector subsystem 32 and imager subsystem 30 to access shared resources on the application server 62, to communicate with one another via the application server 62, and/or to be controlled via the application server 62. For example, software on the application server 62 may be used to coordinate with software on the source and detector subsystems to provide access to shared resources in the system 10 or a network environment. This software may be implemented such that the detector subsystem 32 and imager subsystem 30 appear, to a user, to be directly connected.

In an embodiment, the application server 62 may execute software that provides a multi-user operating system. It will be appreciated that in this case the operating system may be a "network operating system", as distinguished from a single-user operating system. In such an embodiment, the software on the imager subsystems 30 and detector subsystem 32 and the software on the application server 62 may cooperate with each other to provide access to shared resources on the server and/or subsystems. This may be accomplished by designing the software to use a standardized "protocol" so that different vendors can provide interoperable or exchangeable imager subsystem 30 and/or detector subsystems 32.

It will be appreciated that, in one embodiment, the application server 62 may be provided as a general-purpose computer on which software, such as application server software as described herein, runs. In other embodiments, the application server software may run on virtual computers that may be part of generalized or specialized computers within a medical facility, such as a hospital information system (HIS), a radiology information system (RIS), a picture archiving communication system (PACS), and so forth, that may be joined within a distributed network system (FIG. 3).

Using the NIC 110, the detector subsystem 32 transfers relevant information and data, such as functionally descriptive properties and image data for example, to one or both of the imager subsystem 30 and the application server 62. It will be appreciated that detectors physically integrated within an imaging system with a specific imager subsystem specifically configured for the integrated detector, lack capability to transfer functionally descriptive properties. As such, use of an integrated (i.e., non-autonomous) detector with a different imager subsystem requires extensive configuration of the imaging system. The detector subsystem 32, having the memory 122 and/or storage device 124 configured for storing the functionally descriptive properties that describe a functional characteristic of the detector 22, allows for transfer of the functionally descriptive properties to other components such as the imager subsystem 30 and application server 62. The application server 62 may receive the functionally descriptive properties of the detector subsystem 32 and produce a signal representative of compatibility of a combination of a detector subsystem 32 and an imager subsystem 30 based upon the functionally descriptive properties such as dual energy imaging capability, tomosynthesis imaging capability, single energy capability, matrix size, number and location of defective pixels, read-out speed, calibration data, battery charge, weight and size of the detector 22, image storage capacity, and readiness for use to image, and so forth.

In one embodiment, the detector subsystem 32 transfers image data (such as a signal representative of received attenuated radiation) directly to the imager subsystem 30, such as a digital X-Ray imaging subsystem that includes appropriate hardware, firmware, and/or software to process the image data generated and transferred by the detector subsystem 32 to reconstruct a medical image. As an alternative, the detector subsystem 32 may transfer the image data to the application server 62 where it may be constructed into a medical image, where it may be subsequently transferred to the imager subsystem 30 for construction into an image, or where it may be subsequently transferred to another node (e.g., server or workstation) on the network for storage or processing.

In an embodiment, the detector subsystem 32 may include diagnostic circuitry to test and determine an operational status of the detector subsystem 32, such as battery charge remaining, temperature, and communication link bandwidth. The detector subsystem 32 periodically, or when need arises (such as during an examination procedure), notifies at least one of the application server 62 via the network interconnection 102, or the imager subsystem 30 via the network interconnection 100 of the operational status of the detector subsystem 32. In this manner, an exposure event may be prevented during an examination when the detector subsystem 32 is not ready and/or capable of functioning properly. Likewise, in this manner the application server 62 may track the functional status of a detector subsystem 32 when assigning detector/imager subsystem pairs, generating maintenance schedules or requests, and so forth.

For example, an assessment of the status and/or damage of the detector subsystem 32 may be made when the detector subsystem 32 is powered on and/or while the detector subsystem 32 is in use during an examination. In one such embodiment, the locations and/or number of bad pixels identified in one or more scrub images (e.g., dark or unilluminated images that are acquired but not stored) may be compared with the locations and/or numbers identified in previously acquired scrub images. Such a comparison may be used to update a bad pixel map associated with the detector subsystem 32 and/or may be used to determine if the detector subsystem 32 is over a limit or threshold with respect to bad pixels or data line noise that would prevent the use of detector subsystem 32 in some or all applications. In addition, an increase in the number of bad pixels may be indicative of various electrical problems in the detector. Further, detector failures may be detected during or before an examination by monitoring various voltages, such as $V_{com}$, $V_{on}$, and/or $V_{off}$, before allowing an examination sequence to proceed. Such bad pixel or voltage information may also be provided to an application server, as discussed herein, which may make recommendations, such as for suitable imager/detector subsystem pairings, based on the bad pixel and/or voltage information associated with a detector subsystem 32.

In another embodiment, the patient temperature at a patient contacting surface of the detector subsystem 32 may be monitored. In one such embodiment, the patient temperature is monitored where the detector contacts the patient and may be displayed at the detector subsystem 32 and/or at a computer host. In one embodiment, if the temperature reaches a threshold, the detector subsystem 32 may display or sound a warning and/or may notify the application server to provide suitable warnings to the operators. In another embodiment, if the temperature reaches a given threshold the detector subsystem 32 may automatically power down and/or a notification may be sent to the application server 62 or imager subsystem 30 to prevent further radiation emissions by the imager subsystem 30 or to take other system action as appropriate. In yet another embodiment, these approaches may be combined, i.e., temperature above a first threshold may trigger a warning while temperature exceeding a second threshold may result in the inability to continue imaging operations. Such temperature information may be provided to the application server 62 during the examination, for appropriate action as described above, and/or may be stored or analyzed historically such that the propensity for high temperatures using a detector subsystem 32 may be taken into account in generating imager/detector subsystem pairings for certain applications, such as applications where the detector subsystem 32 will be in contact with the patient.

Likewise, such factors as the strength of a wireless connection and/or the battery charge remaining may be monitored for detector subsystems 32 having such functionalities. For example, the battery charge, wireless signal strength and/or communication throughput may be monitored from the time a detector subsystem 32 is removed from its docking station or other storage location until it is returned. An audible and/or visual indicator may signify when any one of these measures falls below an acceptable level, thus notifying an operator of the situation and allowing the operator to take appropriate action. An indication may also be provided to the application server 62, as discussed herein, which may make recommendations, such as for suitable imager/detector subsystem pairings, based on such charge and/or signal strength information.

In addition, other detector status issues may be monitored and used to assess the use of a detector subsystem in a current or future examination. For example, in one embodiment, a detector is only at full power during image acquisition and otherwise remains at a lower power setting. In such an embodiment, to remove the impact of power transients on image quality, one or more scrubs may be performed by the detector subsystem 32 prior to the detector acquiring a storable image during an examination sequence. Such scrub sequences may be utilized to evaluate the status of the detector subsystem 32 with respect to issues such as broken panels, module bonding, wire breakage, and so forth by means of the dark images obtained during scrubbing. If the results of a scrub sequence indicate problems in the detector subsystem 32, the user may be notified (visually and/or audibly) during an examination to prevent needless exposure of the patient to radiation. In addition, an application server 62 may be notified of the result, which may be taken into account in generating imager/detector subsystem pairings.

Such information may be used to determine functionality of the imager subsystem 30 with the detector subsystem 32 and whether the imager subsystem 30 can continue to utilize the detector subsystem 32 or if the detector subsystem 32 requires repair or replacement. Upon a dissociation of the detector subsystem 32 from the imaging subsystem 10 (due to technician request or detector subsystem 32 failure or power loss for example), a new detector subsystem 32 can be associated with the imaging subsystem 10.

With the foregoing discussion in mind, it will be appreciated that various imaging system combinations may be assembled using different autonomous imager and detector subsystems. However, as previously noted, with traditional imaging systems where the source and detector are configured for use with one another and, possibly, physically integrated, the types of applications (e.g., fluoroscopy, tomosynthesis, angiography, dual-energy imaging, pediatric imaging, and so forth) for which the imaging system is suitable is generally know and static. Indeed, the imaging system may have been designed to perform specific imaging applications, with the detector and source components selected accordingly.

However, in present embodiments it may be possible to combine at least different imager and detector subsystems. To the extent that imaging systems assembled from different autonomous imager and detector subsystems may be suitable for different applications, it may be desirable for a practitioner to determine whether a given imager and detector subsystem is suitable for a desired imaging application. Likewise, it may be desirable for a practitioner to determine if a detector or imager subsystem is operating within acceptable limits and/or has received routine maintenance or upgrades. With these factors in mind, in one embodiment an application server 62 is provided that may allow a practitioner to determine the suitability of a particular combination of imager and detector subsystems for a given application or even to recommend a particular combination of source and detector subsystems for the given application.

Figure 5:
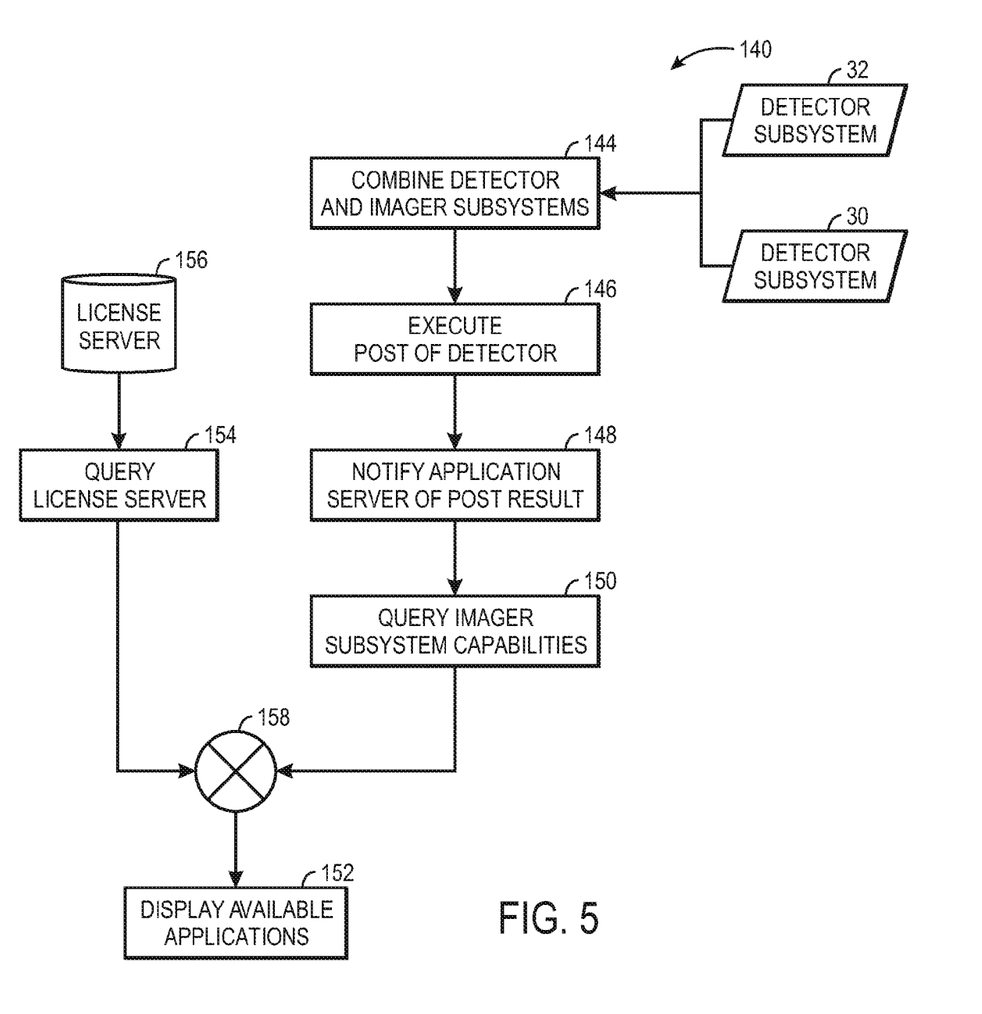
FIG. 5 is a flowchart depicting acts that may be performed in identifying available applications for detector and imager subsystem pairs in accordance with one embodiment.

For example, turning now to FIG. 5, a method 140 is depicted in which a user has selected a detector subsystem 32 and an imager subsystem 30 for use. In one such embodiment, the user may select a portable detector 22 for an examination and may take that detector 22 into an examination room containing an imager subsystem 30. Once in the examination room, the user may activate or register both the detector subsystem 32 and imager subsystem 30 so that an application server in wired or wireless communication with the detector subsystem 32 and imager subsystem 30 recognizes that these systems are going to be combined (block 144) and used together as an imaging system 10. In one embodiment, this may be accomplished by turning on a detector 22 within a room in which an imager subsystem 30 is known to be installed, i.e., activation of the detector 22 in the room is sufficient to indicate that the detector 22 and imager subsystem 30 are going to be used together. In another embodiment, a user may select the desired detector subsystem 32 and imager subsystem 30 from respective interface screens provided by an application server 62, as discussed herein, to indicate the combination of the selected detector subsystem 32 and imager subsystem 30 for use as an imaging system 10.

In FIG. 5, an embodiment is depicted in which the user powers on the selected detector subsystem 32, which executes (block 146) a power-on self test (POST) as part of a detector boot process. As part of the POST, the detector may perform a variety of diagnostic processes, such as performing checks for bad pixels, and so forth, and/or may generate a functional description of the detector subsystem 32, e.g., dimensions, pixels count and density, readout speed, and so forth. The results of the POST may be provided (block 148) to an application server 62 (FIGS. 3 and 4) in network communication with the detector subsystem 32. The application server 62 may elicit (block 150) a functional description of the imager subsystem 30 from the imager subsystem itself or may retrieve such information from a data store within the application server 62 or accessible by the application server 62.

Based on the functional properties of the selected imager subsystem 30 and detector subsystem 32, the application server 62 may determine what types of radiological applications (e.g. fluoroscopy, tomosynthesis, dual-energy imaging, pediatric imaging, and so forth) may be performed using that combination of imager subsystem 30 and detector subsystem 32. A listing of suitable applications for that combination of imager subsystem 30 and detector subsystem 32 may then provided (e.g., displayed) (block 152) to the user and the user may then determine if that combination of imager subsystem 30 and detector subsystem 32 will be suitable.

In one embodiment, the application server 62 may query (block 154) a license server 156 accessible by the application server 62. In such an embodiment, the license server 156 may track the number of licenses an institution or user may have to perform a given application (either concurrently or in a given time period) or may track what device(s) a given application may be performed using. For example, an institution may be limited to performing no more than three concurrent fluoroscopic examination, no more than twenty fluoroscopic examination in a given day (or other interval), or to only perform fluoroscopic examinations with particular detectors, imagers, or detector/imager combinations. In one embodiment, the license server 156 may log the number of times a licensed application is performed and the licensee may be billed based on actual performance of the licensed applications. In such an embodiment a differential price scale may be employed, e.g., the first hundred instances may be billed at rate x while the next hundred instances are billed at rate y. In these examples, the application server 62 may query the license server 156 to determine what applications the selected detector subsystem 32 and imager subsystem 30 may be licensed to perform at the time of the query. The results of the license server query may be combined (block 158) with the detector and imager subsystem functional information to determine and display the available applications that may be performed using the selected detector subsystem 32 and imager subsystem 30 at that time. In such embodiments, the licensed application may be performed on all capable detector and/or imager subsystems, as opposed to being limited to specified systems, with the license server 156 acting to insure the institution or user remains in compliance with the license agreement. As will be appreciated, the license server 156 may also be used to administer trial license arrangements in which the licensee is entitled to perform the licensed application for a limited time or for a limited number of uses.

In FIG. 5, an example of one embodiment is depicted in which a list of possible applications is generated based on what detector subsystem 32 and imager subsystem 30 are selected. In this example, a user may review the list and select an available application to perform using the selected detector subsystem 32 and imager subsystem 30 or may determine whether the selected detector subsystem 32 and imager subsystem 30 are suitable for performing a desired application. If the combination of the detector subsystem 32 and imager subsystem 30 are suitable for the desired application, the user may proceed. If the selected detector subsystem 32 and imager subsystem 30 are not suitable to perform a desired application, the user may select a different detector subsystem 32 or imager subsystem 30 for the application.

By way of example, a user may select an autonomous detector subsystem 32 and may wish to determine the suitability of the selected detector subsystem 32 for a given application. In this example, the specific capabilities of the selected detector may determine the suitability of the detector subsystem 32 for the application. In particular, for detector subsystems that are physically linked with a particular imager system and used for a particular application, detector design and quality control may be directed toward ensuring a uniform, minimal quality for the detector, i.e., all regions of the detector may need to be sufficient to perform a single type of application and/or work with a single imager subsystem. For autonomous detector subsystems that can be combined with different imager subsystems for different applications, this may not be the case. For example, an application such as pediatric imaging may require a detector having low-noise properties suitable for low dose imaging. Conversely, detectors with high numbers of bad pixels or bad pixel clusters may not be suitable for certain applications but may be adequate for others. By way of example, a detector having a bad pixel cluster near its border may be unusable for thoracic imaging (where useful image may extend up to the image border) but may be suitable for extremity imaging where the region of interest is typically centered on the detector. Thus, in certain embodiments, the application server 62 may determine which detectors are best suited for a given application and/or which detectors are not suitable for the application and may return results to the user based upon this determination. In this embodiment, the application server 62 may, based on the detector subsystems 32 that are available and intrinsically capable of performing an application, be able to determine which detector subsystems are best suited for the application, as opposed to those which are not suitable or which are only sufficient for performing the application, but not optimal.

Figure 6:
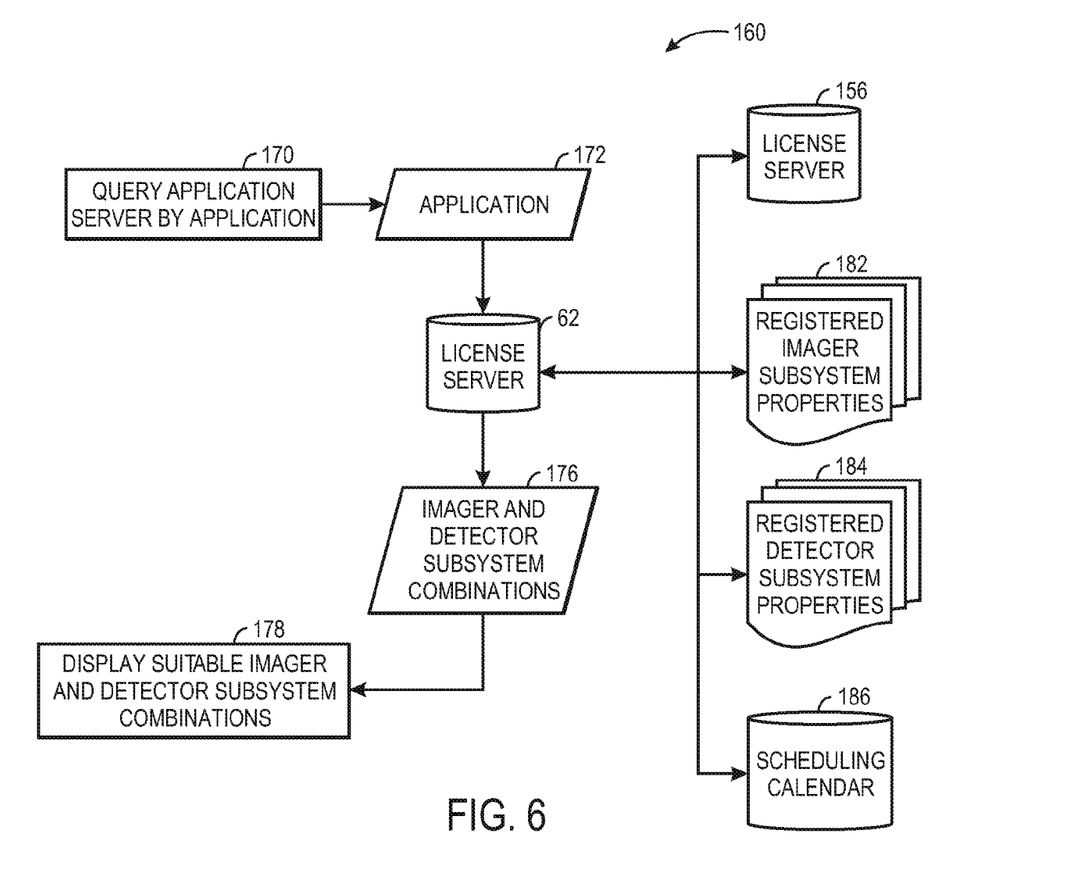
FIG. 6 is a flowchart depicting acts that may be performed in identifying suitable detector and imager subsystem pairs in accordance with one embodiment.

Turning now to FIG. 6, in accordance with another method 160, the user may query (block 170) an application server 62 based on a desired application 172, e.g., tomosynthesis, fluoroscopy, dual-energy, pediatric imaging, and so forth. In some embodiments the user may not specify a detector subsystem 32 or an imager subsystem 30. In other embodiments, the user may also specify one or both of a detector subsystem 32 or an imager subsystem 30.

Based on the desired application 172 and/or a specified imager or detector subsystem, the application server 62 may access one or more databases, lookup tables, or other data stores, to determine what combinations 176 of detector subsystems 32 and/or imager subsystems 30 are available that are suitable for performing the desired application 172. These combinations may be provided to the user, such as by displaying (block 178) a list of the suitable combinations, who may then select an available detector subsystem 32 and/or an imager subsystem 30 that will allow the application 172 to be performed.

For example, in one embodiment the application server 62 may query a list 182 of imager subsystems 30 and/or a list 184 of detector subsystems 32 whose use is administrated by the application server 62. The lists 182, 184 may include information about the respective imager subsystems 30 and detector subsystems 32, such as functional or physical properties such that imager subsystems 30 and/or detector subsystems 32 not suitable for performing the application 172 may be excluded.

For example, if the application 172 is a fluoroscopy application, only imager subsystems 30 and/or detector subsystems 32 suitable for performing fluoroscopy will be returned. In this example, the list 184 of detector subsystems 32 may include a searchable field or other property information for each listed detector subsystem 32 which indicates whether a detector subsystem 32 is capable of high-frame-rate read-out and/or low noise that would allow real-time or fluoroscopic imaging. Detector subsystems 32 that do not allow such rapid image read-out would not be selected by the application server 62 if the application 172 required such rapid read-out, such as a fluoroscopy application. Another example of a detector subsystem property that may be maintained in the list 184 is whether a detector subsystem 32 is capable of image read-out and storage to accommodate tomosynthesis (i.e., acquiring multiple images over a limited angular range). Other detector subsystem properties may include, but are not limited to, the pixel density of the detector, the dimensions or size of the detector, what wavelengths the detector is capable of detecting, whether the detector is suitable for dual-energy imaging, bad pixel maps, maintenance, calibration, and update history, and so forth. Example of properties of the imager subsystems 30 that may be maintained in the list 182 of imager subsystem properties include, but are not limited to, does the source, e.g., X-ray tube, angulate to allow image posting, does the source translate and angulate to enable tomosynthesis acquisitions, is the source suitable for dual-energy imaging (e.g., does the source have suitable kVp switching times), is the source suitable for fluoroscopy, maintenance, calibration, and update history, and so forth. The properties stored in lists 182, 184 may be updated whenever a new detector subsystem 32 or imager subsystem 30 is added to the network, whenever such a subsystem boots up and/or communicates with the network after a change in properties, or in any other suitable arrangement.

As will be appreciated, to the extent that a user may specify an imager subsystem 30 or detector subsystem 32 along with the application 172, only one of the imager subsystems properties list 182 or the detector subsystems properties list 184 may be searched by the application server. For example, if a user specifies an imager subsystem 30 is to be used in performing the application 172, the application server 62 may only search the list 184 of available detector subsystems 32 to determine which ones are suitable for performing the application 172 in conjunction with the specified imager subsystem 30.

If no available detector subsystem 32, imager subsystem 30, and/or combination available detector and imager subsystems 32, 30 are suitable for performing the specified application 172, the application server 62 may notify the user that the application 172 cannot be performed with the imager subsystems 30 or detector subsystems 32 known to application server 62. For example, if the user only specifies the application 172 and the application server 62 determines that no combination of imager and detector subsystems is suitable for performing the application 172, the application server 62 may notify the user that the application 172 cannot be performed using any combination of imager and detector subsystems available to the application server. If the user specified an imager or detector subsystem along with the application 172 and the application server 62 cannot match a corresponding detector or imager subsystem with the specified subsystem to perform the application 172, the application server may notify the user that, based upon the specified imager or detector and the desired application, no available counterpart detector or imager subsystem is suitable for performing the application 172. In such an example, the user may then choose to not constrain the application server 62 to a specific imager or detector subsystem or may specify a different imager or detector subsystem in a subsequent search.

In one embodiment, the application server 62 may also query a license server 156 which tracks the applications licensed by the user in determining what subsystems are available to perform the specified application 172. For example, for certain applications 172, the site may be limited by a license agreement to only performing a certain number of licensed applications in a give time frame (hour, day, week, month, year, and so forth) or may be constrained to perform only a certain number of the licensed applications at one time, i.e., concurrently. Alternatively, as discussed herein, the license server 156 may also track the number of times a licensed application is performed so that the licensee pays on a per-use basis after performance of the application 172. If the user is requesting to perform an application 172 that is subject to a license but for which no license is available (either due to not being purchased or renewed, due to expiration of a trial period, or due to being outside the scope of the license agreement, e.g., too many of the licensed applications have already been performed or are being performed) the application server 62 may notify the user that the application 172 cannot be performed due to license considerations. If, however, the application is within the scope of the license agreement, no such indication may be provided and instead the user may be provided with the detector subsystem 32 and imager subsystem 30 combinations suitable for performing the desired application 172.

In another embodiment, the application server 62 may also query a scheduling calendar 186 or other resource management data store. In such an embodiment, the scheduling calendar 186 may include information about the availability of individual imager subsystems 30, detector subsystem 32, examination rooms, computer or processing resources, radiologists or technicians, and so forth. In addition, in one embodiment, the scheduling calendar 186 may include calibration, upgrade, and/or other maintenance information such that detector or imager subsystems availability or suitability may be dynamically determined based on the performance of scheduled calibrations, maintenance and/or upgrades. Thus, to the extent that the application 172 might be planned at a given day or time, the scheduling calendar 186 may provide information to the application server 62 that may be used to list only those imager subsystems 30 or detector subsystems 32 available at the specified time. Likewise, to the extent that the specified application 172 is to be performed by a technician or radiologist having certain qualifications or training or that specific imager and/or detector subsystems can only be used by certain personnel, the schedules of qualified personnel may be provided to the application server 62 to use in deriving the suitable imager and detector subsystem combinations 176. Likewise, if no suitable imager subsystems 30, detector subsystems 32, and/or qualified personnel are available at the schedule time, the application server 62 may provide this information to a user.

With the foregoing in mind, it will be appreciated that a variety of functions may be provided by the application server 62 in different implementations. For example, the application server 62 may be used to provide resource management infrastructure to a facility or institution (e.g., a hospital, clinic, university, and so forth) to record, track, monitor autonomous imaging system components (i.e., subsystems) as discussed herein. In addition, an application server 62 may allow a user to perform queries based on applications that may be performed by autonomous imaging subsystems or to identify available imaging subsystems that may be used to perform a desired application. Further, an application server 62 may allow recording, tracking, monitoring, and/or querying based on a desired radiological application and on the current and historical state of qualifications, calibrations, capabilities, and changes in capabilities associated with an autonomous detector subsystem or autonomous imager subsystem. Similarly, an application server 62 may allow recording, tracking, monitoring, and/or querying based on a desired radiological application and on available licenses, room or personnel availability, personnel qualifications, and so forth. Likewise, in addition to ad hoc queries based on a selected application and/or imaging system components, as described above, the application server 62 may also be used to generate periodic reports such as of the status, availability, maintenance or calibration needs, changes in performance, and so forth, of imager and/or detector subsystems.

As will be appreciated, the application server 62, as discussed herein, may prevent a user from performing an application 172 that a given combination of imager and detector subsystems are not capable of performing. In this way, the application server 62 may prevent accidental or unnecessary exposure of a patient by preventing exposure events that do not result in useful data due to an unsuitable detector or imager being employed. For example, if the user desired to perform a tomosynthesis application, the application server 62 may prevent the user from combining an suitable imager subsystem 30 with an unsuitable detector subsystem 32, such as a detector subsystem 23 that does not have a suitable read-out rate for tomosynthesis or insufficient memory to store and transmit the number of images prescribed for the tomosynthesis imaging session. In such an example, the application server 62 might not list the proposed detector/imager subsystem combination as an acceptable combination, might warn the user of the unsuitability of the combination using audible or visible indicators, and/or might prevent the unsuitable imager/detector subsystem combination from being exposure enabled, e.g., preventing the imager from emitting radiation when combined with an unsuitable detector. In one embodiment, the application server 62 may also log, track, and/or report instances where administration of an application was prevented due to an improper combination of imager/detector subsystems or due to other factors.

As will be appreciated, an application server 62 and/or the license server 156 as discussed herein may be implemented in various ways. For example, in one embodiment, the application server 62 or the license server may be implemented as a separate and distinct server, utilizing dedicated hardware networked to communicate with detector subsystems 32 and/or imager subsystems 30 over a network infrastructure. Similarly, an application server 62 or license server 156 may be provided as a virtual server that is implemented as a software application operating on an existing devices (e.g., a server, workstation, docking station, detector subsystem, imager subsystem) of a HIS or RIS. Alternatively, an application server 62 or license server may be implemented in a distributed manner, with various aspects of the application server 62 or license server 156 running simultaneously on different devices (e.g., a server, workstation, docking station, detector subsystem, imager subsystem) on a network.

An embodiment of the invention may be embodied in the form of computer-implemented processes and apparatuses for practicing those processes. Embodiments of the present invention may also be embodied in the form of a computer program product having computer program code containing instructions embodied in tangible media, such as floppy diskettes, CD-ROMs, hard drives, USB (universal serial bus) drives, or any other computer readable storage medium, wherein, when the computer program code is loaded into and executed by a computer, the computer becomes an apparatus for practicing the invention. Embodiments of the invention also may be embodied in the form of computer program code, for example, whether stored in a storage medium, loaded into and/or executed by a computer, or transmitted over some transmission medium, such as over electrical wiring or cabling, through fiber optics, or via electromagnetic radiation, wherein when the computer program code is loaded into and executed by a computer, the computer becomes an apparatus for practicing the invention. When implemented on a general-purpose microprocessor, the computer program code segments configure the microprocessor to create specific logic circuits. A technical effect of the executable instructions is to allow use of interchangeable modular detector subsystems and modular imager subsystems independent of one another and in conjunction with an application server on the network.

Technical effects of the present disclosure include detection and notification of detector or imager errors during or prior to an examination sequence in a context where the detector and/or imager operate autonomously. In addition, a technical effect of the present disclosure includes the generation of lists of applications which may be performed using different combinations of autonomous detector and imager subsystems or, conversely, the what combinations of imager and detector subsystems may be utilized to perform a specified application. Another technical effect of the present disclosure includes use of autonomous detector and imager subsystems in a network environment in conjunction with an application server, where the imager subsystem, the detector subsystem, and/or the application server communicate as nodes on the network.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. An imaging management system, comprising:
a network;
a plurality of autonomous imager subsystems, each capable of communicating as respective nodes on the network;
a plurality of autonomous detector subsystems, each capable of communicating as respective nodes on the network and configured for storing functionally descriptive properties that describe a functional characteristic of the detector subsystem; and
an application server capable of communicating as a node on the network, wherein the application server receives the functionally descriptive properties of the detector subsystems and stores and executes routines that generate combinations of imagers and detectors from the plurality of autonomous imager subsystems and the plurality of autonomous detector subsystems based on a type of radiological examination to be performed, wherein the compatibility of a combination of an imager and a detector is at least based upon the functionally descriptive properties.

2. The imaging management system of claim 1, wherein the application server comprises a physical server device.

3. The imaging management system of claim 1, wherein the application server comprises a virtual server implemented as routines executed on one or more devices on the network.

4. The imaging management system of claim 1, wherein the routines that generate combinations of imagers and detectors communicate with a license server in generating combinations of imagers and detectors.

5. The imaging management system of claim 1, wherein the routines that generate combinations of imagers and detectors communicate with a scheduling calendar in generating combinations of imagers and detectors.

6. The imaging management system of claim 1, wherein the routines that generate combinations of imagers and detectors communicate with the plurality of autonomous detector subsystems to determine one or more of the operational parameters, functional status, maintenance history, or calibration status of each detector subsystem.

7. The imaging management system of claim 1, wherein the routines that generate combinations of imagers and detectors communicate with the plurality of autonomous imager subsystems to determine one or more of the operational parameters, functional status, or maintenance history of each imager subsystem.

8. The imaging management system of claim 1, wherein the application server stores and executes a routine that lists the generated combinations of imager and detectors based on the type of radiological examination to be performed.

9. The imaging management system of claim 8, wherein the routine that lists the generated combinations of imager and detectors also describes one or more operational parameters of the listed imagers and detectors.

10. An imaging management system, comprising:
a network;
a plurality of autonomous imager subsystems, each capable of communicating as a node on the network;
a plurality of autonomous detector subsystems, each capable of communicating as a node on the network and configured for storing functionally descriptive properties that describe a functional characteristic of the detector subsystem; and
an application server capable of communicating as a node on the network, wherein the application server receives the functionally descriptive properties of the detector subsystems and stores and executes routines that determine and indicate types of radiological examinations that can be performed by different combinations of imagers and detectors from the plurality of autonomous imager subsystems and the plurality of autonomous detector subsystems, wherein the compatibility of a combination of an imager and a detector is at least based upon the functionally descriptive properties.

11. The imaging management system of claim 10, wherein the application server stores and executes a routine that lists the types of radiological examinations that can be performed by different combinations of imagers and detectors.

12. The imaging management system of claim 10, wherein the routines that determine and indicate the types of radiological examinations that can be performed by different combinations of imagers and detectors determine the types of radiological examinations that can be performed by an imager and/or detector specified by an operator.

13. The imaging management system of claim 12, wherein the application server stores and executes a routine that lists the types of radiological examinations that can be performed by the imager and/or detector specified by the operator.

14. The imaging management system of claim 10, wherein the routines that determine and indicate types of radiological examinations communicate with a license server in determining the types of radiological examination that can be performed by a respective imager or a respective detector.

15. The imaging management system of claim 10, wherein the routines that determine and indicate types of radiological examinations communicate with a scheduling calendar in determining the types of radiological examination that can be performed by a respective imager or a respective detector.

16. The imaging system of claim 10, wherein the routines that determine and indicate types of radiological examinations communicate with the plurality of autonomous detector subsystems to determine one or more of the operational parameters, functional status, maintenance history, or calibration status of each detector subsystem.

17. The imaging system of claim 10, wherein the routines that determine and indicate types of radiological examinations communicate with the plurality of autonomous imager subsystems to determine one or more of the operational parameters, functional status, or maintenance history of each imager subsystem.

\* \* \* \* \*